United States Patent [19]

Lenz et al.

[11] 4,042,636
[45] * Aug. 16, 1977

[54] METHOD FOR THE PREPARATION OF ALCOHOL-FREE ALKALI AND ALKALINE EARTH METAL ALCOHOLATES

[75] Inventors: Arnold Lenz, Cologne-Stammheim; Walter Rogler, Bonn, both of Germany

[73] Assignee: Dynamit Nobel Aktiengesellschaft, Troisdorf, Germany

[*] Notice: The portion of the term of this patent subsequent to Aug. 3, 1993, has been disclaimed.

[21] Appl. No.: 631,263

[22] Filed: Nov. 12, 1975

Related U.S. Application Data

[63] Continuation of Ser. No. 482,977, June 25, 1974, Pat. No. 3,971,833.

[30] Foreign Application Priority Data

July 2, 1973    Germany ............................. 2333634

[51] Int. Cl.$^2$ ............................................. C07C 29/00
[52] U.S. Cl. ................................................. 260/632 A
[58] Field of Search ..................................... 260/632 A

[56] References Cited

U.S. PATENT DOCUMENTS

| 3,317,437 | 5/1967 | Hoffman et al. | 260/632 A |
| 3,520,940 | 7/1970 | Smith | 260/632 A |
| 3,657,361 | 4/1972 | Lenz et al. | 260/632 A |

OTHER PUBLICATIONS

Dupont "Sodium Products Bulletin," undated.

*Primary Examiner*—Joseph E. Evans
*Attorney, Agent, or Firm*—Burgess, Dinklage & Sprung

[57] ABSTRACT

A process for the preparation of an alcohol-free alkali or alkaline earth metal alcoholates dissolved in inert solvent which comprises contacting at least an equimolar amount of an alkali or alkaline earth metal dissolved in an inert solvent with an alcohol at an elevated pressure and at a temperature of at least that at which crystal alcohol splits off from the corresponding alkali or alkaline earth metal alcoholate and below the temperature at which said alcoholate decomposes under the prevailing pressures.

1 Claim, No Drawings

METHOD FOR THE PREPARATION OF ALCOHOL-FREE ALKALI AND ALKALINE EARTH METAL ALCOHOLATES

This is a continuation of application Ser. No. 482,977, filed June 25, 1974, now U.S. Pat. No. 3,971,833.

BACKGROUND OF THE INVENTION

1. Field of the Invention

This invention relates to the preparation of an alcohol-free alkali or alkaline earth metal alcoholate. More particularly, this invention relates to the preparation of an alcohol-free alkaline or alkaline earth metal alcoholate dissolved in an inert solvent. This invention particularly relates to the preparation of such a composition wherein the alkali or alkaline earth metal alcoholate is present in the inert solvent at a high purity.

2. Discussion of the Prior Art

It is known to prepare metal alcoholates from free metals and monovalent alcohols. Depending upon the extent to which the metals employed are divided, the reaction proceeds more or less violently, particularly when using potassium or sodium. The reaction is less violent the longer the chain length of the alcohol is. Primary alcohols react the fastest, the tertiary alcohols reacting the slowest. It is also known to decrease the reaction rate by use of diluents such as, for instance, ether and benzene. (Houben-Weyl VI/2 (1963), page 7). The alkali metal alcoholates prepared in this manner frequently contain 1 to 3 mols of crystal alcohol. Crystal alcohol refers to alcohol molecules in a crystal structure. The crystal alcohols can be removed from the alkali metal alcoholates by heating the composition in hydrogen or in a nitrogen stream or by azeotropic distillation.

It is also known to prepare sodium ethylate free from crystal alcohol by use of a sodium wire which is covered by a small layer of ether. The wire is contacted with the calculated amount of absolute alcohol which is added dropwise to the wire. After about 24 hours the development of hydrogen is terminated. Potassium ethylate can be prepared in the same manner.

It is also known to prepare alkali metal alcoholates free from crystal alcohol by first finely dividing the alkali metal and disposing the same in boiling xylene by means of vigorous stirring. The reaction mixture is thereafter cooled and to the same there is added, drop by drop, the calculated amount of alcohol which is mixed with twice the volume of xylene. The reaction mixture is stirred. This reaction is carried out in a thick-walled vessel, equipped with an agitator, reflux condenser and dropping funnel. The reaction heat produced by the reaction must be removed continuously in order to prevent the reaction from running away. (Houben-Weyl VI/2 (1963), page 8).

These known processes are difficult to control, in particular when they are performed on an industrial scale. Another disadvantage resides in the fact that the metal which is used must initially be ground into a finely divided state. This obviously requires an additional processing step.

In this manner it is possible to prepare alcoholates of a number of primary, lower or higher monovalent alcohols in a crystal alcohol-free state, e.g., of methyl, ethyl, n-propyl alcohol or butanol-(1). However, by this method it has thus far not been possible to prepare alcoholates from reaction of iso-alcohols or carbinols, secondary or tertiary lower or higher alcohols, e.g., isopropyl alcohol, butanol-(2), 2-methyl propanol-(1), 2-methyl-propanol-(2), or the isomeric amyl alcohols, such as pentanol-(2), pentanol-(3), 2-methyl-butanol-(3), 2-methyl butanol-(2), 2-methyl-butanol-(1), 2,2-dimethyl propanol-(1) on an industrial scale with an economically reasonable reaction time and without excessive additional processing steps.

It is also known to prepare potassium tertiary butylate by contacting potassium dust with excessive amounts of tertiary butyl alcohol over a reaction period of about 8 hours with subsequent distillation of the alcohol. However, in this process a product containing crystal alcohol results (cf. Houben-Weyl VI/2 (1963), page 9). In order to remove the crystal alcohol, the dry residue is heated in an oil bath to 200°–220° C. An alcohol free potassium tertiary butylate is obtained in the form of a white granular-crystalline sublimate.

Thus far, it has not been possible to prepare, in direct synthesis, an alcohol-free alkali or alkaline earth metal alcoholate dissolved in a hydrocarbon or hydrocarbon mixture. For instance, it has not thus far been possible to obtain, in direct synthesis, a hydrocarbonaceous mixture containing an alkali or alkaline earth metal alcoholate of an iso-alcohol, carbinol, secondary or tertiary alcohol. In order to prepare such solutions it has thus far been necessary to first free an alcohol-containing alcoholate prepared by the above described methods or an alcohol-containing alcoholate by re-alcoholizing an alkali metal alcoholate of a lower primary alcohol with a higher iso-alcohol, carbinol, secondary alcohol or tertiary alcohol from crystal alcohol by thermal treatment. This thermal treatment is then followed by dissolving the now alcohol-free alcoholate in the inert solvent.

Alkali and alkaline earth metal alcoholates are known to be of substantial use in the chemical industry. Especially the pure crystal alcohol-free alkali or alkaline earth metal tertiary butylate is used increasingly more as a condensation agent. The reason for this is due to the fact that the tertiary butylate anion is an especially strong proton acceptor and the released sterically hindered tertiary butyl alcohol does not in most instances cause any side reactions.

Owing to the increased handling safety and accurate reaction controls, it has become advantageous to use alcohol-free alkali and alkaline earth metal alcoholates dissolved in inert solvents.

It is, therefore, an object of the present invention to provide a process by which an alcohol-free alkali and alkaline earth metal alcoholate dissolved in inert solvents can be prepared which process can be performed by a direct process without involving the initial preparation of an alcohol-containing alkali or alkaline earth metal alcoholate followed by separation of the alcohol therefrom and a dissolution of the alcohol-free alcoholate in inert solvent.

It is therefore an object of the present invention to provide such a direct process which characterize the heretofore known processes unencumbered by the disadvantages.

SUMMARY OF THE INVENTION

The objects of the present are satisfied by a process for the preparation of an alcohol-free alkali or alkaline earth metal alcoholate dissolved in an inert solvent which process comprises contacting at least an equimolar amount of an alkali or alkaline earth metal dissolved in an inert solvent with an alochol at an elevated pressure and at a temperature of at least that at which crystal alcohol splits off from the corresponding alkali or alkaline earth metal alcoholate and below the temperature at which said alcoholate decomposes under the prevailing pressure.

It has been discovered, therefore, that an inert solvent containing an alcoholate of an alkali or alkaline earth metal can be provided in a simple essentially one-step process by initially contacting at least an equimolar amount of alkali or alkaline earth metal, while dissolved in an inert solvent, with the alcohol and regulating the temperatures of the reaction such that there is utilized a temperature above that at which crystal alcohol splits off from the corresponding alcoholate and below that at which the corresponding alcoholate decomposes. The reaction is generally performed at increased pressures.

The temperatures employed are preferably from 5°–10° C above the temperature at which crystal alcohol splits off at normal pressure. Generally speaking, the process is conducted at temperatures between 160° C and 210° C, preferably between 180° C and 190° C. It will be realized, however, that the temperature will depend upon the particular alcohol reactant and the decomposition point of the corresponding alcoholate. The extent to which increased pressure is employed depends upon the temperature selected.

Essentially, a pressure equivalent to autogenous pressure is suitable.

The process of the present invention involves the reaction of the alkali or alkaline earth metal while the same is maintained in a solvent. Generally speaking, the alkali or alkaline earth metal is present in such solvent in an amount between 1% and 10% by weight.

According to the invention the alkali or alkaline earth metal is present in the reaction mixture in at least an equimolar amount relative to the amount of alcohol to be employed. Preferably, the alkali or alkaline earth metal is present in a molar excess especially a molar excess between 5% and 15%.

The method of the present invention provides exceptionally high yields of the corresponding metal alcoholate. Moreover, the metal alcoholate is present in the inert solvent at high degrees of purity, especially purities of at least > 99%. Stated differently, it has been found that the amount of alcohol containing metal alkali or alkaline earth metal alcoholate in the inert solvent is less than 0,01%, particularly less than 0,001%, based upon the weight of the entire composition.

The procedure of the present invention is particularly useful in the preparation of those alcoholates which have heretofore proven to be prepared only with great difficulty. Thus, the present invention is particularly directed to the preparation of alkali and alkaline earth metal alcoholates of iso-alcohols, carbinols, secondary lower or higher mono-valent alcohols and tertiary lower or higher monovalent alcohols, in particular, the preparation of tertiary butyl alcoholates or tertiary amyl alcoholates, e.g., alkali or alkaline earth metal alcoholates of 2-methyl-butanol-(2). It is to be understood, however, that the method of the present invention can be used to prepare those alcoholates of primary alcohols that are soluble in the inert solvents employed. Generally speaking, alcoholates of alkali or alkaline earth metals can be prepared from alcohols having a chain length of $C_1$ to $C_{24}$ carbon atoms, especially $C_1$ to $C_8$ carbon atoms.

For the process according to the invention, hydrocarbons or hydrocarbon mixtures are used as inert solvents, in which the alcoholate formed is soluble. Thus, for instance, a mixture consisting of cyclohexane and toluene, e.g., at a ratio of 10:1, is used to prepare the sodium tertiary butylate. For the preparation of potassium tertiary butylate, for instance, p-xylene can be used. Higher boiling benzines, e.g., those having a boiling point of 120°–140° C, can also be used. In general, those solvents or solvent mixtures are suitable that do not have any functional groups with respect to alkali metals or alkaline earth metals or their alcoholates. For instance, aromatic substances such as xylene, toluene and the like or cycloaliphatic hydrocarbons such as cyclohexane or aliphatic hydrocarbons for instance, hexane, benzines and the like as well as their mixtures are suitable.

The concentration of the alcoholate formed in the solution or the solvent mixture depends upon the maximum solubility of the alcoholates in the solvents. It is therefore advisable to first determine the solubility and to adjust the quantitative ratio of the alcohol used to the inert solvent accordingly.

The term "alkali or alkaline earth metal" is understood to also include their hydrides.

The reaction components can be brought into contact for instance in a stirring autoclave by stirring or, for instance, in a pipe or circulation reactor by pumping. The pressure vessels used should be provided with a cooling and heating device.

At the beginning of the reaction, in particular in the case of primary lower alcohols such as, for instance, methyl or ethyl alcohol, the reaction according to the invention can be carried out under normal pressure. In that case it is advisable to equip the reactor with a reflux condenser or the like. It is also advisable in that case, i.e., in the case of violently reacting reaction components, to introduce the metal stepwise in portions. At the point at which insoluble alcohol-alcoholate adducts have formed in the inert solvent or solvent mixture, the reaction slows down markedly, since the surface of the metal used is deactivated by the insoluble products formed. At this point the reaction vessel should be closed and the reaction temperature should be increased to the temperature range according to the invention.

When reacting slower-reacting reaction participants, for instance, when using relatively long-chain primary or iso-alcohols or carbinols or secondary or tertiary alcohols having more than 2 carbon atoms at the molecule, it is advisable to heat the mixture to the required temperature under pressure right from the beginning of the reaction. When preparing, for instance, tertiary butylates and tertiary amylates, it is not necessary to introduce the metal used by portions or to reduce the metal used to a finely divided state in a separate process step before bringing it into contact with the alcohols.

When preparing sodium or potassium tertiary butylate, the reaction mixture is for instance heated in a closed pressure vessel to a temperature of at least 160° C., the splitting off temperature of the crystal alcohol under normal pressure. Preferably the mixture is heated to a temperature of approximately 165° to approximately 170° C. When working at 165° C, if a cyclohexane-toluene mixture (weight ratio 10:1) is used, a pressure of 10 kp per square centimeter is realized when the concentration of the alcohol in the solvent mixture is 10% by weight. Upon continuing the reaction, the pressure rises as a result of the released hydrogen. This pressure can be maintained during the duration of the reaction by continuously drawing off the hydrogen. It may, however, also be proceeded in such a way that the hydrogen is collected in the reaction vessel until the reaction is terminated and only then it is drawn off. In the case of sodium or potassium tertiary amylate the splitting off temperature of the crystal alcohol (at normal pressure) is 165° C.

When working in p-xylene, a pressure of 3 kp per square centimeter is realized for a concentration of the alcohol in the solvent of 10% by weight.

The method according to the invention can also be carried out continuously by passing, for instance, the reaction solution through several reactors connected in series, which are charged with the alkali or alkaline earth metals.

One of the advantages of the method according to the invention is the fact that, compared to the heretofore known processes in which relatively slow reacting alcohols are used, the reaction times are considerably shorter although, contrary to the known process, it is not necessary to reduce the metal used to a finely divided state in an additional process step prior to the actual reaction. Rather, the alkali or alkaline earth metal can be introduced into the reaction vessel in the form of relatively larger lumps without any further prior comminution, e.g., of particular size 100 to 1000 microns.

A further advantage of the method according to the invention is that alcohol-free solutions of alcoholates of relatively slow reacting alcohols, in particular of isoalcohols or carbinols or of secondary or tertiary alcohols, can be prepared directly in an essentially one-step process. After releasing the hydrogen, the solution containing the alcoholate can be separated from the excess metal simply by decanting. The excess metal which is obtained consists more or less of large agglomerated beads after the reaction is completed or rather after the reaction mixture has cooled off. Generally speaking, the reaction is conducted for between 60 and 120 minutes depending on the reactants.

The solutions of alcohol-free alcoholates in inert solvents prepared by the method according to the invention are characterized by a high degree of purity with respect to the alcoholate. They are safe to handle and are suitable for use in a variety of chemical reactions. They can, for instance, be used in condensation, addition or polymerization reactions or in the preparation of alkali or alkaline earth metal derivatives of organic compounds. It is advantageous to use the solutions prepared in accordance with the invention in those chemical reactions in which a solution of an alcohol in an inert solvent results, e.g., for release of an alkoxy group of the alcoholate in the form of an alcohol. By the method of the invention, one can simply and by direct synthesis work up these alcohol-containing solutions to yield the corresponding alcoholate containing solutions.

A further advantage of the method according to the invention as compared to the heretofore known methods lies in the fact that it is not imperative to free the alcohol used for the reaction completely from water in a previous process step. Thus, one can use a composition which has a concentration of alcohol of 96% by volume without adversely affecting the purity of the dissolved alcoholate if an excess of metal corresponding to the water content is used. The resulting hydroxide is insoluble in the inert solvent and it is easy to separate, for instance, by filtration. But even when using completely anhydrous reaction participants, an excess of metal based on the quantity of alcohol used, is preferably used.

It is surprising that undesirable side reactions as they are observed, for instance, when reacting silicon with alcohols (cf. Houben-Weyl VI/2 (1963), page 100) where the split off hydrogen reacts with the alcohol at increased temperatures to form alkanes and water, do not occur in the process according to the invention.

Alcoholates are known to be relatively sensitive to heat; at elevated temperatures decomposition phenomena may occur, especially at temperatures in excess of 210° C.

As a result of the increased pressures applied in the process according to the invention, it had to be expected that the temperature, at which the crystal alcohol is split off from the alcoholate, would be considerably higher than when working at normal pressure. Surprisingly enough, however, in spite of the increased pressure, the crystal alcohol is split off at approximately the same temperature as under conditions of normal pressure. That means that the reaction can be carried out at temperatures at which a decomposition of the resulting alcoholates is avoided.

The alcoholates prepared by the process according to the invention are free from alcohol; they can be prepared at a degree of purity of 99%.

In a given case it can be advisable to carry out, in the process according to the invention, the charging and discharging of the reaction vessel under a protective gas curtain in order to prevent possible contaminations resulting from the action of atmospheric air.

Additionally, the alcoholate-containing solution can be evaporated to the dry state, for instance under reduced pressure, if both an alcohol-free alcoholate and an alcoholate free from inert solvents is to be obtained.

In order to more fully illustrate the nature of the invention and the manner of practice of same, the following Examples are presented:

EXAMPLE 1

23 g of metallic sodium (1 mole) in a mixture consisting of 600 g (7.15 moles) of cyclohexane, 65 g (0.71 moles) of toluene and 65 g (0.88 moles) of tertiary butyl alcohol are placed into an agitator autoclave (capacity: 2 ltr.) and are heated to 170° C while stirring, the pressure rising during the entire operating time of 1.5 hours to a constant value of 18 kp per square centimeter. After cooling, a residual pressure of 8.5 kp per square centimeter remained, resulting from the hydrogen formed.

Following the release of 9.8 ltr. of hydrogen, a clear solution of 11.8% by weight of sodium tertiary butylate in a mixture of cyclohexane and toluene was obtained.

The yield, based on the hydrogen formed, was 99.7% of theory.

The excess of metallic sodium used was obtained in the form of an agglomerated bead at the bottom of the reaction vessel.

EXAMPLE 2

30 g (0.77 mole) of metallic potassium in a mixture of 800 g (7.55 moles) p-xylene and 52 g (0.7 mole) of tertiary butyl alcohol are placed in the same apparatus as in Example 1 and are heated to 170° C while stirring. Within the entire operating time of 1.5 hours the pressure rose to a constant value of 11 kp per square centimeter. After cooling, a residual pressure of 8.1 kp per square centimeter remained, resulting from the hydrogen formed.

The yield, based on the hydrogen formed, was 99.2% of theory.

Following the release of 8 ltr. of hydrogen, a clear solution of 9.1% by weight of potassium tertiary butylate in xylene was obtained.

EXAMPLE 3

22 g (0.96 mole) of metallic sodium in a mixture of 800 g (approximately 7.15 moles) of benzine (boiling point 120°–140° C) 72 g (0.68 mole) of tertiary amyl alcohol (2-methyl butanol-(2)) are placed into the same apparatus as in Examples 1 and 2 and are heated to 175° C. Within the entire operating time of 1.5 hours the pressure rose to a constant value of 12 kp per square centimeter. After cooling, a residual pressure of 9.5 kp per square centimeter remained, resulting from the hydrogen formed. After release of 9.2 ltr. of hydrogen, a clear solution of 10.1% by weight of sodium tertiary amylate in benzine was obtained.

The yield, based on the hydrogen formed, was 99.5% of theory.

The excess of sodium used was obtained as agglomerated bead at the bottom of the reaction vessel.

The alcoholate solutions prepared in accordance with Examples 1–3 were free from alcohol. Upon addition of only one drop of alcohol to the clear solutions, an adduct alcohol/alcoholate, which was insoluble in the solvent or solvent mixture, was formed.

What is claimed is:

1. A process for the preparation of an alcohol-free alkali or alkaline earth metal alcoholate in an inert hydrocarbonaceous solvent which comprises contacting at least an equimolar amount of an alkali radical or alkaline earth metal in an inert hydrocarbonaceous solvent, which solvent is inert to said alkali or alkaline earth metal, with a monovalent $C_1$–$C_{24}$ alkanol at an elevated pressure in a closed vessel and at a temperature of at least that at which crystal alcohol split off from the corresponding alkali or alkaline earth metal alcoholate under normal pressure and below the temperature at which alkali or alkaline earth metal alcoholate decomposes under the prevailing pressure.

* * * * *

UNITED STATES PATENT AND TRADEMARK OFFICE
CERTIFICATE OF CORRECTION

PATENT NO. : 4,042,636
DATED : August 16, 1977
INVENTOR(S) : Arnold Lenz et al

It is certified that error appears in the above-identified patent and that said Letters Patent are hereby corrected as shown below:

Title page, "Notice:", change "Aug. 3, 1993" to --

July 27, 1993 --

Col. 2, line 68, change "alochol" to -- alcohol --.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*